(12) United States Patent
Nakamura

(10) Patent No.: US 10,574,756 B2
(45) Date of Patent: Feb. 25, 2020

(54) ELECTRONIC DEVICE, SELECTION CONTROL SYSTEM, SELECTION METHOD, AND RECORDING MEDIUM

(71) Applicant: CASIO COMPUTER CO., LTD., Tokyo (JP)

(72) Inventor: Masaru Nakamura, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 181 days.

(21) Appl. No.: 15/639,644

(22) Filed: Jun. 30, 2017

(65) Prior Publication Data

US 2018/0007138 A1 Jan. 4, 2018

(30) Foreign Application Priority Data

Jul. 4, 2016 (JP) .................................. 2016-132684
May 11, 2017 (JP) .................................. 2017-094317

(51) Int. Cl.
*H04L 29/06* (2006.01)
*H04L 29/08* (2006.01)
(Continued)

(52) U.S. Cl.
CPC .......... *H04L 67/12* (2013.01); *A63B 24/0062* (2013.01); *A63B 71/0622* (2013.01);
(Continued)

(58) Field of Classification Search
CPC ............ A63B 71/0622; A63B 24/0062; A63B 2230/06
(Continued)

(56) References Cited

U.S. PATENT DOCUMENTS 7,996,177 B2 * 8/2011 Tatsuta ................. A61B 5/0002
702/150
10,143,405 B2 * 12/2018 Jayalath ............... A61B 5/0022
(Continued)

FOREIGN PATENT DOCUMENTS

JP 2006-293535 A 10/2006
JP 2009-88989 A 4/2009
(Continued)

OTHER PUBLICATIONS

"Wearable Sensor-Based Rehabilitation Exercise Assessment for Knee Osteoarthritis"—Chen et al, Department of Biomedical Engineering, National Yang-Ming University, Feb. 12, 2015 (Year: 2015).*
Japanese Office Action dated Jun. 11, 2019, in a counterpart Japanese patent application 2017-094317. (A machine translation (not reviewed for accuracy) attached.).

*Primary Examiner* — Randy A Scott
(74) *Attorney, Agent, or Firm* — Chen Yoshimura LLP

(57) ABSTRACT

An electronic device includes: a memory; and a processor connected to the memory and configured to receive signals from a plurality of sensors that detect an activity state of a user wearing, or having in its vicinity, the electronic device, wherein the processor reads out a program stored in the memory to perform the following processes: receiving the signals from the plurality of sensors; determining the activity state of the user based on the received signals; selecting one or more of sensors from the plurality of sensors on the basis of the determined activity state; deriving, on the basis of the determined activity state, information to be communicated to the user, the information to be communicated to the user being derived from the signals from the selected one
(Continued)

or more of the sensors; and causing the derived information to be communicated to the user.

15 Claims, 10 Drawing Sheets

(51) Int. Cl.
*A63B 71/06* (2006.01)
*A63B 24/00* (2006.01)
*G06F 1/16* (2006.01)

(52) U.S. Cl.
CPC ...... *H04L 67/42* (2013.01); *A63B 2071/0663* (2013.01); *A63B 2220/12* (2013.01); *A63B 2220/17* (2013.01); *A63B 2220/44* (2013.01); *A63B 2220/72* (2013.01); *A63B 2220/74* (2013.01); *A63B 2220/75* (2013.01); *A63B 2220/803* (2013.01); *A63B 2220/805* (2013.01); *A63B 2220/808* (2013.01); *A63B 2220/836* (2013.01); *A63B 2220/89* (2013.01); *A63B 2230/06* (2013.01); *A63B 2230/30* (2013.01); *A63B 2230/50* (2013.01); *A63B 2230/75* (2013.01); *G06F 1/163* (2013.01)

(58) Field of Classification Search
USPC ........ 709/203, 204, 205, 219; 600/300, 301, 600/391
See application file for complete search history.

(56) References Cited

U.S. PATENT DOCUMENTS

| | | | |
|---|---|---|---|
| 2002/0068873 A1* | 6/2002 | Nissila | A61B 5/02438 600/509 |
| 2006/0230108 A1 | 10/2006 | Tatsuta et al. | |
| 2011/0213225 A1* | 9/2011 | Bernstein | G06Q 50/22 600/309 |
| 2012/0182939 A1* | 7/2012 | Rajan | A61B 5/0008 370/328 |
| 2015/0006617 A1 | 1/2015 | Yoo et al. | |
| 2016/0269806 A1* | 9/2016 | Uchiumi | H04Q 9/00 |

FOREIGN PATENT DOCUMENTS

| | | |
|---|---|---|
| JP | 2014-192735 A | 10/2014 |
| JP | 2015-011699 A | 1/2015 |

* cited by examiner

Input Data Table (Exercise States)

| |
|---|
| Walking |
| At rest |
| Specific arm movement |
| Running |
| Riding a bike |
| Riding in a car |
| Riding a train |
| Riding other type of vehicle |
| ... |

Input Data Table (External Environment)

| |
|---|
| On a road |
| Mountain |
| Lake |
| Ocean |
| Altitude increasing/decreasing by X m/hr or more |
| ... |

Activity State Determination Table

| Exercise State \ External Environment | On a road | Mountain | Lake | Ocean | Altitude increasing/decreasing by X m/hr or more | ... |
|---|---|---|---|---|---|---|
| Walking | Walking | Hiking | ✗ | ✗ | Hiking | |
| At rest | Resting | Resting | Resting | Resting | Resting | |
| Specific arm movement | ✗ | Fishing | Fishing | Fishing | ✗ | |
| Running | Running | Trail running | ✗ | ✗ | Trail running | |
| Riding a bike | Cycling (on road) | Cycling (MTB) | ✗ | ✗ | Cycling (MTB) | |
| Riding in a car | Vehicle movement | Vehicle movement | ✗ | ✗ | Vehicle Movement | |
| Riding a train | Vehicle movement | Vehicle movement | Vehicle movement | Vehicle movement | Vehicle Movement | |
| Riding other type of vehicle | | Cable car, lift, etc. | Water sports | Water sports | | |
| ... | | | | | | |

Sensor Information Selection Table $\quad$ 122b

| Activity State | Display Information 1 | Display Information 2 |
|---|---|---|
| Walking | No. of steps | Calories burned |
| Running | Speed | Calories burned |
| Hiking | Altitude | Compass |
| Trail running | Altitude | Heart rate |
| Cycling (road bike) | Speed | Heart rate |
| Cycling (MTB) | Speed | Altitude |
| Fishing | Weather | Atmosphere |
| Water sports | Weather | Temperature |
| Resting | OFF | OFF |
| Vehicle movement | Speed | Weather |

FIG. 4B

ELECTRONIC DEVICE, SELECTION CONTROL SYSTEM, SELECTION METHOD, AND RECORDING MEDIUM

BACKGROUND OF THE INVENTION

Technical Field

The present invention relates to an electronic device, a selection control system, a selection method, and a recording medium.

Background Art

Conventionally, there is a technique in which a mobile telephone including a plurality of sensors obtains a number of steps, a movement distance, and so on of a user and notifies the user of that information, as is disclosed in Japanese Patent Application Laid-Open Publication No. 2009-88989.

SUMMARY OF THE INVENTION

However, there are now more types of sensors due to recent advances in mobile telephones, tablets, and the like, and thus the user must carry out operations for selecting a sensor each time the user checks desired sensor information. Such selection operations are extremely burdensome.

Having been achieved in light of such a problem, it is an object of the present invention to enable a user to check desired sensor information without burdening the user. Accordingly, the present invention is directed to an electronic device that substantially obviates one or more of the problems due to limitations and disadvantages of the related art.

Additional or separate features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, in one aspect, the present disclosure provides an electronic device, including: a memory; and a processor connected to the memory and configured to receive signals from a plurality of sensors that detect an activity state of a user wearing the electronic device, wherein the processor reads out a program stored in the memory to perform the following processes: receiving the signals from the plurality of sensors; determining the activity state of the user based on the received signals; selecting one or more of sensors from the plurality of sensors on the basis of the determined activity state; deriving, on the basis of the determined activity state, information to be communicated to the user, the information to be communicated to the user being derived from the signals from the selected one or more of the sensors; and causing the derived information to be communicated to the user.

In another aspect, the present disclosure provides a system for exchanging information between a server and a wearable electronic device via a network, including: the server having a first memory and a first processor; and the electronic device wearable by a user and including a second memory; a second processor connected to the second memory, and a plurality of sensors that detect an activity state of the user wearing the electronic device, wherein in the server, the first processor reads out a program stored in the first memory to execute the following processes: receiving signals from the electronic device representing signals detected by the plurality of sensors; determining the activity state of the user based on the received signals; selecting one or more of sensors from the plurality of sensors at the electronic device on the basis of the determined activity state of the user; transmitting to the electronic device the selection of the one or more of the sensors, wherein in the electronic device, the second processor reads out a program stored in the second memory to execute the following processes: generating the signals detected by the plurality of sensors; transmitting the signals representing the signals detected by the plurality of sensors to the server; receiving from the server the selection of the one or more of the sensors; causing information sensed by the selected one or more of the sensors to be communicated to the user.

In another aspect, the present disclosure provides a method for selectively communicating sensed information to a user by a wearable electronic device, the electronic device having a memory; a processor connected to the memory, and a plurality of sensors that detects an activity state of the user, the method including, via the processor: receiving signals from the plurality of sensors; determining the activity state of the user based on the received signals; selecting one or more of sensors from the plurality of sensors on the basis of the determined activity state; deriving, on the basis of the determined activity state, information to be communicated to the user, the information to be communicated to the user being derived from the signals from the selected one or more of the sensors; and causing the derived information to be communicated to the user.

In another aspect, the present disclosure provides a non-transitory storage medium having stored therein instructions executable by a processor in a wearable electronic device having a plurality of sensors that detects an activity state of a user, the instructions in the storage medium causing the processor to perform the following: receiving signals from the plurality of sensors; determining the activity state of the user based on the received signals; selecting one or more of sensors from the plurality of sensors on the basis of the determined activity state; deriving, on the basis of the determined activity state, information to be communicated to the user, the information to be communicated to the user being derived from the signals from the selected one or more of the sensors; and causing the derived information to be communicated to the user.

In another aspect, the present disclosure provides an electronic device, including: a memory; and a processor connected to the memory and configured to receive a plurality of types of information respectively sensed by a plurality of sensors that detect an activity state of a user wearing, or having in its vicinity, the electronic device, wherein the processor reads out a program stored in the memory to perform the following processes: receiving the plurality of types of information respectively sensed by the plurality of sensors; determining the activity state of the user based on the received plurality of types of information; selecting one or more of the plurality of types of information on the basis of the determined activity state; and causing said selected one or more of the plurality of types of information to be communicated to the user.

According to the present invention, a user can check desired sensor information without being burdened. It is to be understood that both the foregoing general description and the following detailed description are exemplary and explanatory, and are intended to provide further explanation of the invention as claimed.

BRIEF DESCRIPTION OF THE DRAWINGS

FIG. 3A is a diagram illustrating an example of the data structure of an input data table (exercise state).

FIG. 3B is a diagram illustrating an example of the data structure of an input data table (external environment).

FIG. 4A is a table indicating an activity pattern table used to predict an activity according to an embodiment.

FIG. 4B is a table indicating combinations of sensor information set in accordance with activity patterns.

DETAILED DESCRIPTION OF EMBODIMENTS

An embodiment of the present invention will be described hereinafter with reference to the drawings.

Figure 1:
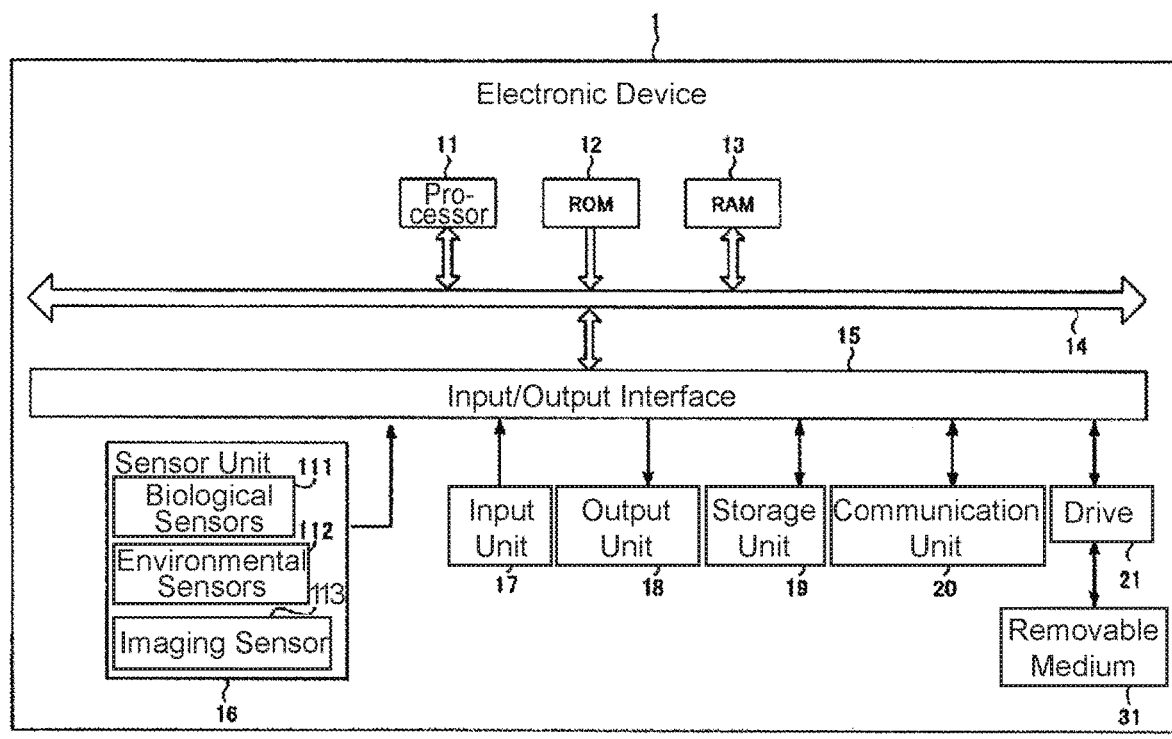
FIG. 1 is a block diagram illustrating the hardware configuration of an electronic device according to an embodiment of the present invention.

FIG. 1 is a block diagram illustrating the hardware configuration of an electronic device 1 according to an embodiment of the present invention.

The electronic device 1 is configured as a mobile terminal such as a smartphone or a smartwatch.

The electronic device 1 includes a processor (central processing unit) 11, read-only memory (ROM) 12, random access memory (RAM) 13, a bus 14, an input/output interface 15, a sensor unit 16, an input unit 17, an output unit 18, a storage unit 19, a communication unit 20, and a drive 21.

The processor 11 executes various types of processing in accordance with programs recorded in the ROM 12 or programs loaded into the RAM 13 from the storage unit 19.

Data and so on required by the processor 11 to execute the various types of programs is stored in the RAM 13 as appropriate.

The processor 11, the ROM 12, and the RAM 13 are connected to each other by the bus 14. The input/output interface 15 is also connected to the bus 14. The sensor unit 16, the input unit 17, the output unit 18, the storage unit 19, the communication unit 20, and the drive 21 are connected to the input/output interface 15.

The sensor unit 16 includes biological sensors 111, environmental sensors 112, and an imaging sensor 113. The biological sensors 111 include a six-axis accelerometer capable of detecting movement directions, a gyrosensor capable of detecting orientation, a magnetic sensor capable of detecting a combination of rotation and heading, and a plurality of sensors that measure biological information such as pulse (heartbeat), blood pressure, and body temperature. The biological information measured here is stored in the storage unit 19. The environmental sensors 112 include a plurality of sensors that measure environmental information of the environment where the user is present, such as location, temperature, barometric pressure, humidity, ultraviolet light amount, and noise. For example, a GPS unit that receives GPS signals from a plurality of GPS satellites through a GPS reception antenna is provided, and environmental information measured by the environmental sensors 112 is stored in the storage unit 19.

The imaging sensor 113 includes an optical lens unit and an image sensor (not illustrated), and obtains biological information and environmental information of the user by analyzing details of a captured image. The activity state of the user can be determined more precisely by, for example, detecting how vigorous the user's activity is from the blurriness of a captured image, or, in the case where a river or an ocean appears in the image, determining that the user is near water.

The optical lens unit is constituted by lenses that focus light, such as a focus lens and a zoom lens, in order to capture an image of a subject. The focus lens is a lens that forms a subject image on a light-receiving surface of the image sensor. The zoom lens is a lens that freely changes the focal length within a set range. The optical lens unit also includes peripheral circuits for adjusting setting parameters such as focus, exposure, and white balance as necessary.

The image sensor is constituted by a photoelectric conversion element, an analog front end (AFE), and so on. The photoelectric conversion element is constituted by a complementary metal oxide semiconductor (CMOS) photoelectric conversion element or the like, for example. The subject image from the optical lens unit is incident on the photoelectric conversion element. The photoelectric conversion element photoelectrically converts (captures) the subject image and accumulates an image signal for a set amount of time, and sequentially supplies the accumulated image signal to the AFE as an analog signal.

The AFE executes various signal processes, such as an analog/digital (A/D) conversion process, on the analog image signal. A digital signal is generated as a result of the various signal processes, and this digital signal is outputted as an output signal from the imaging sensor 113. The output signal from the imaging sensor 113 will be called "captured image data" hereinafter. The captured image data is supplied as appropriate to the processor 11, an image processing unit (not illustrated), and so on.

The input unit 17 is constituted by various buttons, a touch panel provided with a display, and so on, and inputs various information in response to instruction operations made by the user.

The output unit 18 is constituted by a display, a speaker, and the like, and outputs video, audio, and so on.

The storage unit 19 is constituted by a hard disk or dynamic random access memory (DRAM), and stores various types of image data.

The communication unit 20 is configured to be capable of communicating with external devices/external terminals using near-field wireless communication such as Bluetooth (trade name) Low-Energy (BLE), or a wireless LAN (local area network) via IEEE 802.11, for example.

A removable medium 31, such as a magnetic disk, an optical disk, a magneto-optical disk, or a semiconductor memory, is mounted in the drive 21 as appropriate. Programs read out from the removable medium 31 through the drive 21 are installed in the storage unit 19 as necessary. Furthermore, various types of data stored in the storage unit 19, such as image data, are stored in the removable medium 31 in the same manner as in the storage unit 19.

FIGS. 2A to 2D are schematic diagrams illustrating examples of a display pattern in the output unit 18 according to the embodiment of the present invention.

As illustrated in FIGS. 2A to 2D, the electronic device 1 according to the present embodiment is configured to notify the user of necessary information in accordance with the user's activity state by displaying such information in a display region 181 and a display region 182.

Note that in the present embodiment, a smartwatch is used as an example of the electronic device 1, and thus the configuration is such that regions used for chronographs when displaying the time are used as the display region 181 and the display region 182 in order to display sensor information.

Using the data of the biological information of the user obtained by the biological sensors 111 and the data of the external environment obtained by the environmental sensors 112, the processor 11 determines the user's exercise state and external environment from the input data table illustrated in FIGS. 3A and 3B, which will be described later. However, the configuration may be such that the user's exercise state and external environment are determined using the data of the biological information of the user and the data of the external environment obtained by the imaging sensor 113 as well.

Using the user's exercise state and external environment determined here, the user's activity state is determined from an activity state determination table, which is illustrated in FIG. 4A and will be described later, and the sensor information is selected on the basis of a sensor information selection table, which is illustrated in FIG. 4B and will be described later. Then, the necessary sensor information can be notified to the user in accordance with the user's activity state by displaying the selected sensor information in the display region 181 and the display region 182 illustrated in FIG. 2A.

For example, in the case where the user's activity state is determined to be "walking" by using the user's exercise state data and external environment data to refer to the activity state determination table illustrated in FIG. 4A (described later), sensor information of "number of steps" and "calories burned" is selected from the sensor information selection table.

Figure 2A:
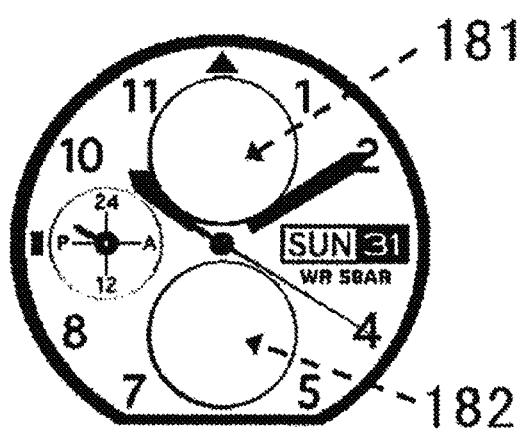
FIG. 2A is a diagram illustrating an example of a display pattern in the electronic device according to an embodiment of the present invention.
Figure 2B:
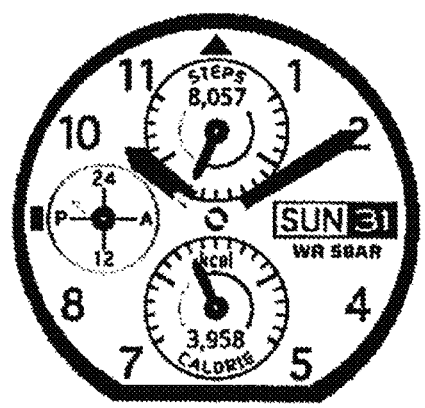
FIG. 2B is a diagram illustrating an example of a display pattern in the electronic device according to an embodiment of the present invention.
Figure 2C:
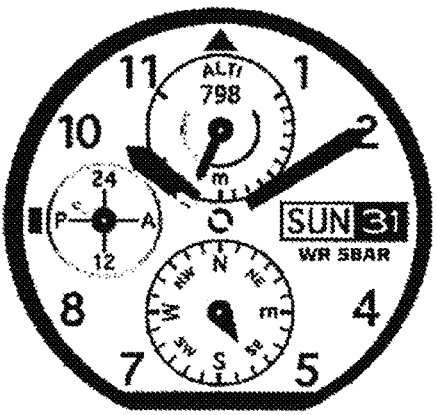
FIG. 2C is a diagram illustrating an example of a display pattern in the electronic device according to an embodiment of the present invention.

Then, as indicated by the display state illustrated in FIG. 2B, the sensor information is notified to the user by displaying the "number of steps" information in the display region 181 and the "calories burned" information in the display region 182 indicated in FIG. 2A.

Figure 2D:
FIG. 2D is a diagram illustrating an example of a display pattern in the electronic device according to an embodiment of the present invention.

The display format of the output unit 18 is not limited to simultaneously display with analog hands as indicated in FIG. 2A. For example, the configuration is such that the display process is possible even in the case where a digital display without hands is carried out, as illustrated in FIG. 2D.

Additionally, although FIG. 2A indicates a configuration in which two display regions are set within the region of the output unit 18, the configuration is not limited thereto. The configuration may be such that even more display regions can be set within the region of the output unit 18.

Such a configuration makes it possible for the user to see more sensor information at once.

FIG. 3A illustrates an example of the data structure of an input data table 121a in which the user's exercise states as determined on the basis of the biological information obtained from the biological sensors 111 are set, and FIG. 3B illustrates an example of the data structure of an input data table 121b set on the basis of the external environment information obtained from the environmental sensors 112.

According to the input data table 121a illustrated in FIG. 3A, the user's exercise state such as "walking" or "at rest" can be obtained from the biological information such as heartbeat, pulse, and an operation log obtained from the biological sensors 111. This information is set in the input data table 121a in the storage unit 19 under the control of the processor 11. Additionally, by holding the environmental information obtained from the environmental sensors 112, or GPS tracking and map data, altitude and other physical attributes for a given piece of location information can be found. For example, it can be determined that the user is currently on a road, or is at a mountain, a lake, an ocean, or the like, and furthermore is at an altitude of greater than or equal to X meters, is in or on a road/a building, is near mountain ABC, is on lake DEF, and the like. This information is set in the input data table 121b of the storage unit 19 under the control of the processor 11.

FIG. 4A illustrates an example of the data structure of an activity state determination table 122a held in the storage unit 19, and FIG. 4B illustrates an example of the data structure of a sensor information selection table 122b also held in the storage unit 19. FIG. 4A is a table constituted by a matrix of the exercise states and external environments held in the input data table, and is used to determine the user's current activity state. FIG. 4B, meanwhile, is a table used to select a combination of the sensor information (display information 1 and display information 2) needed by the user for a given activity state. Both are determined or predicted from the exercise state set in the input data tables 121 (the input data table 121a) and the external environment (the input data table 121b).

According to the activity state determination table 122a in FIG. 4A, when the exercise state in the input data table 121a is "walking" and the external environment in the input data table 121b is "on a road," the user's activity state can be determined to be "walking." When the exercise state is "walking" and the external environment is "mountain" or "altitude change of greater than or equal to X m/hr," the user's activity state can be determined to be "hiking." This determination is made by the processor 11. Meanwhile, when the exercise state in the input data table 121a is "at rest," the user's activity state is determined to be "resting" regardless of the external environment in the input data table 121b. Additionally, in the case where the exercise state in the input data table 121a is "specific arm movement" and the external environment in the input data table 121b is "mountain," "lake," or "ocean," the user's activity state is determined to be "fishing."

In the activity state determination table 122a illustrated in FIG. 4A, the "x" signs indicate activity patterns that cannot normally arise.

However, this is only an example, and the activity patterns applicable to the present invention are not limited to those indicated in the activity pattern determination table 122a. The configuration may be such that any desired activity patterns can be input in the locations marked by an "x."

The sensor information selection table 122b illustrated in FIG. 4B is a table for selecting sensor information according to the activity state. In other words, when the determined or predicted activity state of the user is "walking," it is assumed that the sensor information needed by the user is "number of steps" and "calories burned," and thus the setting is such that these two pieces of data are notified to the user Likewise, in the case where the activity pattern is determined to be "running," it is assumed that the sensor information needed by the user is "speed" and "calories burned," and thus the setting is such that these two pieces of data are notified to the user.

Additionally, when the user's activity state is "fishing," it is assumed that the sensor information needed by the user is "weather" and "barometric pressure," and thus the setting is such that these two pieces of data are notified to the user. Although combinations of sensor information needed by the user are set in the sensor information selection table 122b illustrated in FIG. 4B in advance, the configuration may be such that these combinations can be set by the user as desired. Such a configuration makes it possible to more reliably notify the user of the sensor information needed by the user.

In the above-described configuration, in the case where sensor information appropriate for the user's activity state has been selected in the sensor information selection table 122b, the electronic device 1 may start up the sensors needed to obtain the selected sensor information and stop the sensors that are not needed.

Additionally, in the above-described configuration for sensor control, the process of selecting and notifying the sensor information to the user is repeated, and thus the configuration may be such that the sensors needed for determining the user's activity state are not stopped even when those sensors are not needed to obtain the selected sensor information.

Figure 5:
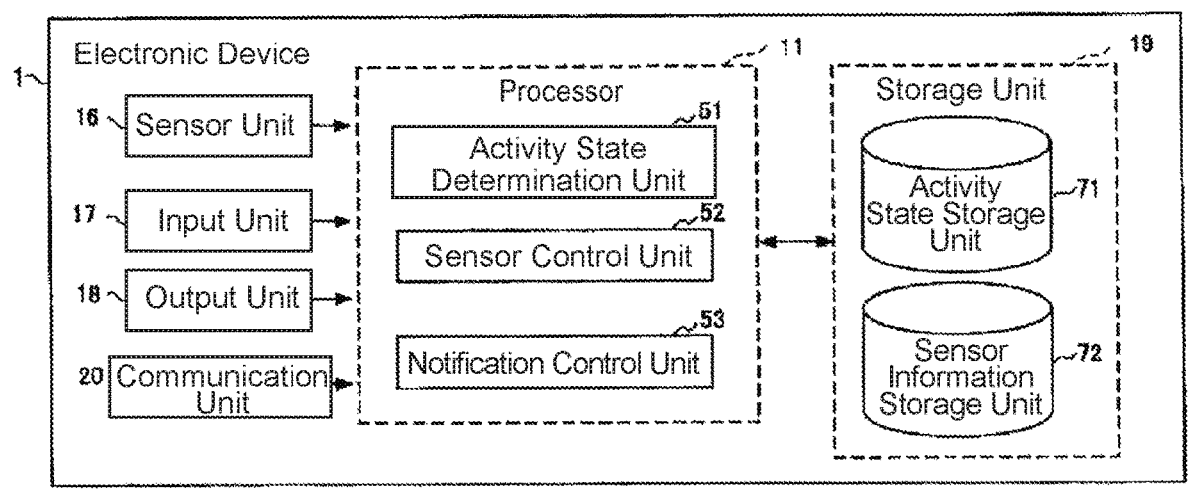
FIG. 5 is a block diagram indicating functions involved in a notification process according to the present invention.

FIG. 5 is a function block diagram illustrating a functional configuration, of the overall functional configuration of the electronic device 1, that is used to execute the notification process.

The "notification process" is a sequence of processes for notifying the user of the information needed by the user from among the information obtained by the electronic device 1 from the sensors, the exterior, and so on in the case where the user's activity state has been estimated.

The "notification process" includes an "activity state determination process based on a movement state and environmental information" and a "sensor information selection process based on the activity state."

When executing the notification process, an activity state determination unit 51, a sensor control unit 52, and a notification control unit 53 function so as to carry out a process for notifying the user, as indicated in FIG. 5.

Additionally, an activity state storage section 71 and a sensor information storage section 72 are provided in regions of the storage unit 19.

The activity state storage section 71 stores the activity state determination table 122a or determining the user's activity state on the basis of the sensor information obtained from the sensor unit 16, and stores information pertaining to trends in the results of determining the user's activity state.

The sensor information storage section 72 stores the sensor information selection table for selecting the sensor information to be notified to the user in accordance with the user's activity state, and stores change information, corresponding to a case where the user has changed a stored combination of the sensor information, as change trend information of the user.

The activity state determination unit 51 analyses the state of the electronic device 1 on the basis of the sensor information obtained by the sensor unit 16, and determines the activity state of the user carrying the electronic device 1 on the basis of the activity state determination table stored in the activity state storage section 71.

The sensor control unit 51 carries out control so as to start up the sensors needed to obtain the sensor information corresponding to the user's activity state as determined by the activity state determination unit 51, and stop the sensors unrelated to the activity state determination.

The notification control unit 53 obtains, from the sensor information storage section 72, the sensor information corresponding to the user's activity state as determined by the activity state determination unit 51, and outputs/reports that sensor information through the output unit 18.

The operations of the electronic device 1 (the notification process) according to Embodiment 1 of the present invention, which has been described with reference to FIGS. 1 to 5, will be described in detail hereinafter with reference to the flowcharts in FIGS. 6 and 7. Note that the steps described hereinafter can be realized by the program being executed by a computer.

(Basic Operations)

Figure 6:
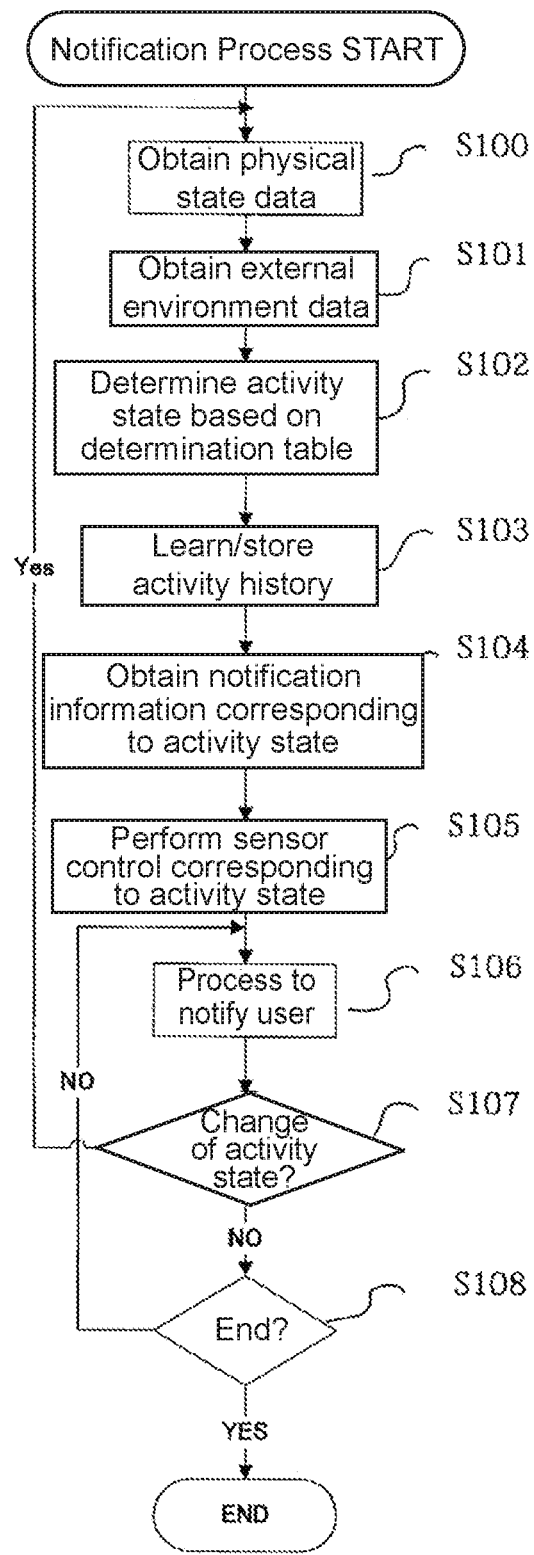
FIG. 6 is a flowchart illustrating the overall flow of a sensor information selection process.
Figure 7:
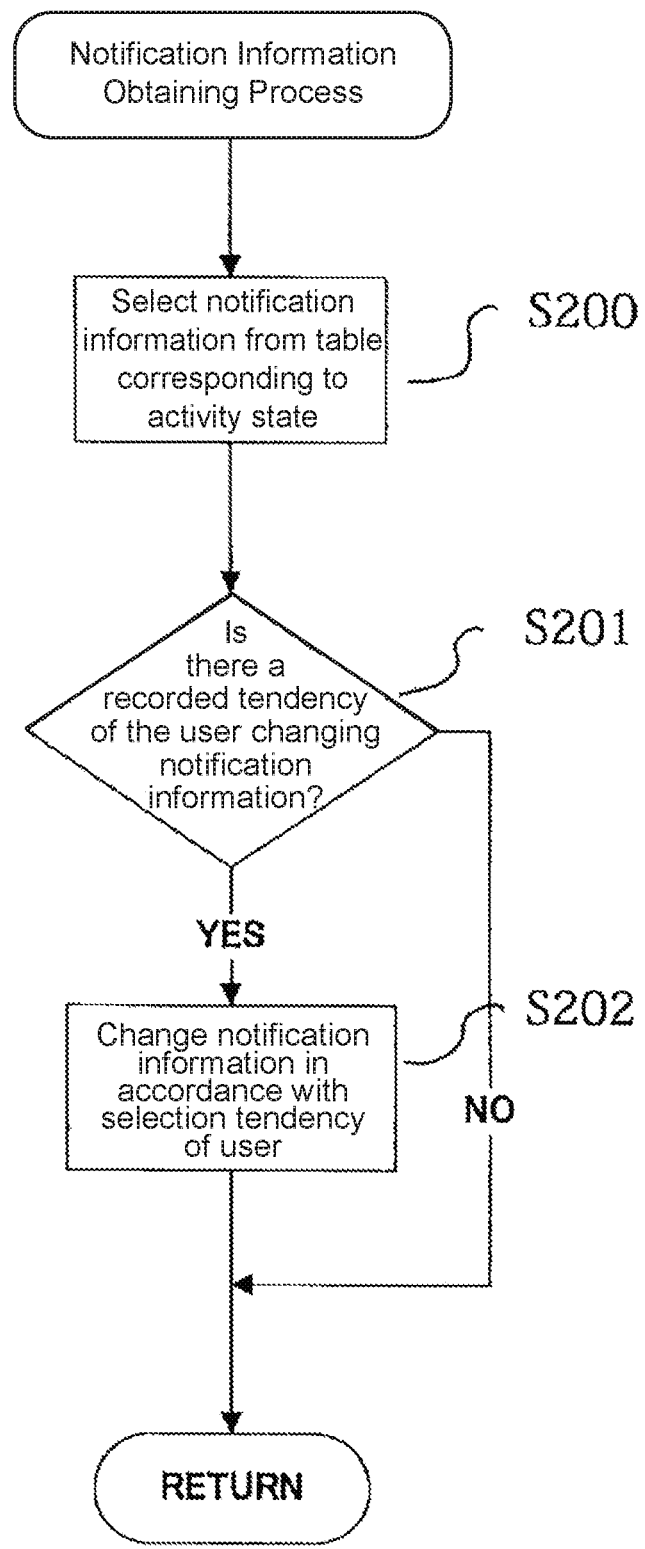
FIG. 7 is a detailed flowchart pertaining to a part of the flowchart in FIG. 6 where sensor information appropriate for an activity state is obtained.

FIG. 6 illustrates the basic operations of the electronic device 1 according to the embodiment of the present invention as a flowchart. As illustrated in FIG. 6, in the electronic device 1 according to the embodiment of the present invention, the biological sensors 111 of the sensor unit 16 detect the user's physical state data (biological information), which is then obtained by the processor 11 and sent to the activity state determination unit 51 (step S100). Next, the environmental sensors 112 detect external environment data (environmental information), which is then obtained by the processor 11 and passed to the activity state determination unit 51 (step S101). At this time, the activity state determination unit 51 also obtains other data, such as GPS data, detected by the environmental sensors 112. Note that the biological information and environmental information may be measured and obtained in any order, and it is assumed here that the information is obtained in the order it is detected by the sensors.

The activity state determination unit 51 of the processor 11 determines the user's activity state on the basis of the activity state determination table 122a held in the activity state storage section 71 (step S102). In this determination, the activity state determination unit 51 searches the activity states and environmental information in the input data tables 121a and 121b for data appropriate for the user's state, on the basis of the biological information and environmental information obtained from the sensor unit 16. Then, the activity state determination table 122a is searched on the basis of the exercise state and external environment detected from the input data tables 121. For example, in the case where the exercise state set in the input data table 121a is "walking" and the external environment set in the input data table 121b is "on a road," the activity state determination unit 51 determines that the user's activity state is "walking" on the basis of the activity state determination table 122a.

Next, the activity state determination unit 51 executes a learning process on the activity history, on the basis of the determination result (step S103). The activity state determination unit 51 carries out control such that the learning result is applied to similar activity patterns held in the activity pattern determination table 122a, and the results are stored as the user's activity trends. In other words, the activity history is updated in sequence in accordance with the user's activities, and a more accurate prediction is carried out by referring to the activity trends in which the activity states have been updated.

Next, the notification control unit 53 receives the determination result from the activity state determination unit 51, and carries out a process for selecting the sensor information corresponding to the determined activity state of the user (step S104).

The specific flow of processing will be described later using the flowchart in FIG. 7.

After the process for selecting the sensor information carried out by the notification control unit 53, a sensor control process for the sensor unit 16 is carried out by the sensor control unit 52 so as to start up the sensors needed in the notification process and stop the sensors not needed in the notification process (step S105).

For example, the sensor control unit 52 starts up the sensors needed in the notification process on the basis of the sensor information selected by the notification control unit 53. Furthermore, it is confirmed whether or not unnecessary sensors unrelated to the obtainment of the selected sensor information and unrelated to the activity state determination are operating, and in the case where it is determined that unnecessary sensors are operating, those unnecessary sensors are stopped.

The notification control unit 53 makes a notification to the user by outputting the sensor information selected in step S104 through the output unit 18 (step S106).

For example, the notification control unit 53 displays the selected sensor information in the display regions 181 and 182 on the display, as illustrated in FIG. 2B, so as to notify the user of the necessary sensor information in accordance with the user's activity state.

After the process of notifying the user, the activity state determination unit 51 determines whether or not there has been a change in the user's activity state on the basis of the sensor information from the sensor unit 16 (step S107).

In the case where it is determined in step S107 that there has been a change in the user's activity state, the process returns to step S101 and the notification process is carried out again.

However, in the case where it is determined in step S108 that there has been no change in the user's activity state, the process advances to step S108.

In step S108, it is determined whether or not an operation for ending the notification process has been detected.

For example, the electronic device 1 ends the notification process in the case where an operation for ending the notification process has been inputted to the input unit 17 by the user, the case where no operation inputs have been made by the user and no movement information of the user has been detected for a long period of time, or the like.

In the case where no such ending operation is detected, the process returns to step S106.

(Sensor Information Selection Process)

The flow of the process through which the notification control unit 53 selects the sensor information in accordance with the user's activity state will be described in detail with reference to the flowchart illustrated in FIG. 7.

First, the sensor information is selected in accordance with the user's activity state as determined by the activity state determination unit 51 in step S102 (step S200).

For example, the notification control unit 53 selects the sensor information in accordance with the user's activity state as determined, by referring to the sensor information selection table 122b stored in the sensor information storage section 72. For example, in the case where the user's activity state is determined to be running, "speed" and "calories burned," which are the combination of sensor information corresponding to running, are selected from the sensor information selection table 122b.

Next, it is determined whether or not a history of changes made by the user is stored for the selected combination of sensor information (step S201).

For example, the notification control unit 53 refers to the sensor information storage section 72 to confirm the presence/absence of information pertaining to a change history indicating whether or not the user has carried out a process for changing the sensor information, for the selected combination of sensor information.

The process advances to step S202 in the case where it is determined that the above-described change history is stored.

However, the process returns to the basic operation flow in the case where it is determined that the above-described change history is not stored.

In step S202, the notification control unit 53 changes the combination of the sensor information in accordance with the history of the changes to the sensor information made by the user.

For example, the notification control unit 53 refers to the history of the changes to the sensor information made by the user, changes a predetermined combination of sensor information to the combination of sensor information changed by the user, and returns to the basic operation flow.

According to the above-described configuration, in the electronic device 1 according to the embodiment of the present invention, the activity state determination unit 51 selects the sensor information appropriate for the user's activity state by referring to the activity state storage section 71 in which the activity states are stored, and outputs the selected sensor information to the output unit 18. As such, the information needed by the user according to the user's activity state can be automatically presented to the user. Accordingly, the necessary information for a variety of user activities can be obtained automatically, without placing the burden of manually selecting the needed information from a variety of pieces of information on the user.

In the present embodiment, the configuration is such that a predetermined combination of sensor information is changed to the combination of sensor information changed by the user, by referring to the history of changes made to the sensor information by the user. However, the configuration may be such that a combination of sensor information for which a change history is not recorded is changed to a combination of sensor information matching the user's preferences, in accordance with the change history recorded for another combination of sensor information.

For example, the configuration may be such that in the case where the combination of "number of steps" and "calories burned," which corresponds to "walking," is frequently changed to "number of steps" and "temperature" by the user, a combination of "speed" and "temperature" may be used and notified to the user in the case where the user's activity has been determined to be "running."

In the present embodiment, the configuration is such that the user's activity state is detected, the sensor information to be notified to the user is selected and displayed, and upon another change in the activity state being detected, the sensor information that is notified to the user is switched. However, the configuration is not limited thereto.

For example, the configuration may be such that once the user's activity state is detected and the sensor information to be notified to the user is selected and displayed, changes in the user's activity state are not detected for a set amount of time.

In the present embodiment, the configuration is such that the combination of sensor information corresponding to the determined activity state is displayed. However, the configuration may be such that some or all of the displayable sensor information is displayed and the sensor information corresponding to the activity state is displayed with emphasis.

For example, the configuration may be such that of multiple pieces of sensor information being displayed, the display region for the sensor information corresponding to the user's activity state is displayed with a greater surface area than the other sensor information, is displayed with a higher brightness than the other sensor information, or is displayed in a position that stands out more than the other sensor information (in the center or top of the display region, for example).

In the present embodiment, the configuration may be such that the sensor unit 16 includes biological sensors and environment sensors having different levels of precision. For example, the configuration may be such that in the case where the user's activity state that has been determined is an activity state for which it is desirable to display highly-accurate sensor information, the sensor information obtained by a more precise sensor is preferentially displayed. Likewise, the configuration may be such that in the case where the user's activity state that has been determined is an activity state for which it is desirable to use a sensor that consumes less power, the sensor information obtained by a sensor that is less precise by consuming less power is preferentially displayed.

The configuration may be such that a change in the user's activity state is notified to the user using sounds or lights.

For example, the configuration may be such that in the case where it has been determined that the user's activity state has changed from "walking" to "running," the notification that the user's activity has changed and the sensor information being notified to the user has changed is carried out using a voice saying "the activity state has changed" or by emitting light from a light-emitting member provided in the electronic device.

In the present embodiment, the configuration is such that sensors not needed to obtain the sensor information selected on the basis of the user's activity state are stopped. However, the configuration may be such that the frequency at which the sensors obtain information (the sensing frequency) is reduced rather than stopping the sensors.

In the present embodiment, the output unit is configured such that the sensor information is notified to the user by displaying the sensor information in a display. However, the configuration is not limited thereto, and may be such that the user's desired sensor information is outputted as voice from an included speaker.

In the present embodiment, the configuration is such that the above-described functions are implemented by a single electronic device. However, the configuration may be such that the above-described processing is carried out among multiple devices, where the sensor information obtained by the electronic device is sent to a server, the activity state is determined, and the electronic device having the output unit then carries out the process of notifying to the user that sensor information on the basis of the determination result.

In the present embodiment, sensor information corresponding to the determination result from a plurality of types of sensors is selected as the sensor information to be notified to the user, but the sensor information may be transmitted externally via a communication unit.

Figure 8:
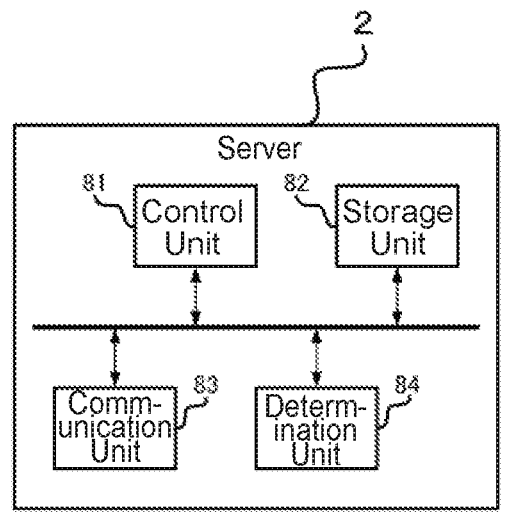
FIG. 8 is a block diagram of a server according to an embodiment of the present invention.

FIG. 8 is a block diagram for executing the activity determination process in the functional configuration of a server 2.

The activity determination process refers to a series of processes that extrapolate the activity of the user from sensor information.

The server 2 includes a control unit 81, storage unit 82, communication unit 83, and a determination unit 84.

As shown in FIG. 8, when executing the activity determination process, the control unit 81, storage unit 82, communication unit 83, and determination unit 84 function to perform the activity determination process for the user.

The control unit 81 includes a processor function and controls data communication in the server 2 among the storage unit 82, communication unit 83, and determination unit 84, and also controls the processes of each unit.

The storage unit 82 is constituted by a hard disk, DRAM (dynamic random access memory), or the like, and stores the input data table 121a configured by the exercise state of the user as determined on the basis of the received biological information, the input data table 121b configured on the basis of the received external environment information, the activity state determination table 122a for determining the activity state of the user based on the received sensor information, and the sensor information selection table 122b that determines the sensor information corresponding to the activity state. The storage unit 82 also stores information pertaining to trends in the user's activity state determination results.

The communication unit 83 is configured to be able to communicate with an external device/external terminal using near-field wireless communication such as BLE (Bluetooth [registered trademark] Low Energy), wireless LAN (local area network) via IEEE 802.11, or the like, for example.

The determination unit 84 analyzes the state of the user from the received sensor information and determines the activity state of the user on the basis of the activity state determination table 122a stored in the storage unit 82.

A process for the selection control system of the present invention will be described in detail below with reference to the sequence diagram in FIG. 9. The respective steps described below can be realized by corresponding programs being executed by a computer.

Figure 9:
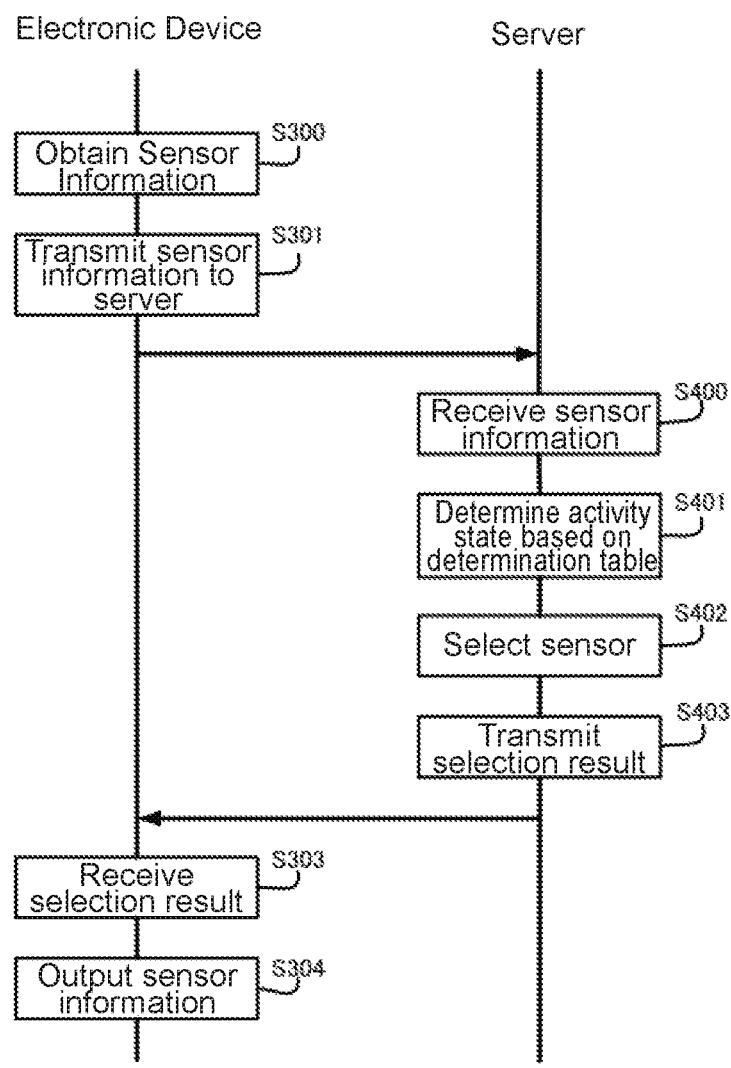
FIG. 9 is a sequence diagram showing a process flow of a selection control system of the present invention.

FIG. 9 shows a flow chart describing the notification process in the electronic device 1 under the selection control system of the present invention. According to FIG. 9, the electronic device 1 under the selection control system of the present invention obtains, as sensor information, physical state data (biological information) of the user from the biological sensors 111 of the sensor unit 16, external environment data (environmental information) from the environmental sensors 112, and data from a GPS etc. (step S300). The measurements of the biological information and environmental information and the order in which the information is obtained is set as desired and is assumed to be the order in which the information is detected by the respective sensors.

Next, the electronic device 1 transmits the obtained sensor information to the server 2 via the communication unit 20 (step S301).

Next, the server 2 receives the sensor information via the communication unit 83 (step S400) and, with the received sensor information, determines via the determination unit 84 the activity state of the user on the basis of the activity state determination table 122a stored in the storage unit 82 (step S401). During determination of the activity state, a search is performed on the basis of the obtained sensor information for data corresponding to the status of the user from the exercise states and external environments shown in the input data tables 121a and 121b. The activity state determination table 122a is then indexed on the basis of the exercise state and external environment detected from the input data tables 121a and 121b.

Next, the server 2 performs a selection process for the sensor information corresponding to the determined activity state of the user (step S402). The obtained sensor selection result is transmitted to the electronic device 1 via the communication unit 83 (step S403).

Next, the electronic device 1 receives the determination result via the communication unit 20 (step S303), and based on the determination result, outputs sensor information corresponding to the determined activity state of the user (step S304). For example, the sensor control unit 52, on the basis of the sensor information selected by the notification control unit 53, starts up the sensors necessary for the notification process. Furthermore, the sensor control unit can verify whether sensors that are unrelated to the obtaining of the selected sensor information and unrelated to activity state determined are running and stop these unnecessary sensors if it is determined that such unnecessary sensors are running.

In the present embodiment, the electronic device 1 and the server 2 communicate information to each other via a network, and changes may be made to processes associated with the electronic device 1 and server 2 in consideration of the communication status of the network. For example, it is assumed that the server 2 performs the selection process for sensor information corresponding to the determined activity state of the user (step S402), but the determination result may be transmitted from the serve 2 to the electronic device 1 and the electronic device 1 may perform the selection process for the sensor information corresponding to the determined activity state of the user based on the received determination result.

Although the present embodiment describes an example in which the display is circular in shape, the shape and size of the display is not limited thereto, and the shape of the display of the output unit 18 may be polygonal or curved.

In the present embodiment, the configuration is such that a plurality of pieces of sensor information are displayed in a single display. However, the configuration is not limited thereto, and in a notification system including a plurality of displays, the configuration may be such that the sensor information is distributed among the plurality of displays.

In the present embodiment, the configuration is such that a plurality of pieces of sensor information are displayed in a single display. However, the configuration is not limited thereto, and the configuration may be such that only one type of sensor information appropriate for the user's activity state is displayed in a single display.

Although embodiments of the present invention have been described thus far, it goes without saying that the technical scope of the present invention is not intended to be limited to the above-described embodiments. It will be clear to one skilled in the art that various changes and improvements can be added to the embodiments described above. That such additions of changes and improvements can also fall within the technical scope of the present invention will be made clear from the content of the scope of the claims.

What is claimed is:

1. An electronic device, comprising:
a memory;
a processor connected to the memory and configured to receive signals from a plurality of sensors that detect an activity state of a user wearing, or having in its vicinity, the electronic device; and
a display unit for displaying information to the user,
wherein the processor reads out a program stored in the memory to perform the following processes:
receiving the signals from the plurality of sensors;
determining the activity state of the user based on the received signals;
selecting one or more of sensors from the plurality of sensors on the basis of the determined activity state;
deriving, on the basis of the determined activity state, multiple pieces of information to be communicated to the user as being associated with the determined activity state of the user, said multiple pieces of information to be communicated to the user being derived from the signals from said selected one or more of the sensors; and
causing said derived multiple pieces of information to be displayed on the display unit,
wherein the display unit has a plurality of display regions respectively displaying said multiple pieces of information on the display unit,
wherein the plurality of sensors include a first sensor that obtains information pertaining to an exercise state of the user and a second sensor that obtains information pertaining to an external environment of the user,
wherein the processor determines the exercise state by selecting one of a plurality of preset exercise states on the basis of the information obtained by the first sensor, said plurality of preset exercise states including at least one of resting, walking, running, and riding a bike,
wherein the processor determines the external environment of the user by selecting one of a plurality of preset external environment states on the basis of the information obtained by the second sensor, said plurality of preset external environment states including at least one of on-a-road, mountain, and altitude increasing-decreasing states,
wherein the processor determines the activity state of the user by selecting one of a plurality of preset activity states on the basis of the selected one of the preset exercise states and the selected one of the preset external environment states, said plurality of preset activity states including at least one of walking, hiking, trail running, cycling on road, and mounting biking,
wherein said plurality of preset exercise states, said plurality of preset external environment states, and said plurality of preset activity states are stored in said memory or a separate memory, and
wherein the processor selects said one or more of sensors from the plurality of sensors on the basis of the determined activity state and derives said multiple pieces of information displayed to the user as being associated with the determined activity state of the user, by referring to a lookup table that defines predetermined associations between the plurality of preset activity states and the multiple pieces of information respectively corresponding thereto, the lookup table being stored in said memory or said separate memory.

2. The electronic device according to claim 1,
wherein the electronic device is configured to receive, from the user, instructions to change said multiple pieces of information displayed to the user associated with the determined activity state of the user, and wherein the processor generates change trend information on the basis of a frequency and/or history of the instructions from the user to change said multiple pieces of information that is associated with the determined activity state of the user, and overrides the lookup table that defines the predetermined associations in accordance with the change trend information so as to cause the user changed multiple pieces of information to be displayed in the display unit for the determined activity state of the user.

3. The electronic device according to claim 1, wherein in selecting said one or more sensors, the processor selects one or more sensors that contributed to the determination of the activity state of the user, and said multiple pieces of information to be communicated to the user corresponds to information sensed by said selected one or more of the sensors.

4. The electronic device according to claim 1, wherein in selecting said one or more sensors, the processor selects one or more sensors that contributed to the determination of the activity state of the user, and the processor derives said multiple pieces of information to be communicated to the user based on information sensed by at least one of said selected one or more of the sensors.

5. The electronic device according to claim 1, further comprising a communication unit,
wherein the processor transmits the derived information from the communication unit to outside via a network.

6. The electronic device according to claim 1,
wherein said plurality of preset exercise states includes all of resting, walking, running, and riding a bike,
wherein said plurality of preset external environment states includes all of on-a-road, mountain, and altitude increasing-decreasing states, and
wherein said plurality of preset activity states includes all of walking, hiking, trail running, cycling on road, and mounting biking.

7. A system for exchanging information between a server and a wearable electronic device via a network, comprising:
the server having a first memory and a first processor; and
the electronic device wearable by a user and comprising a second memory; a second processor connected to the second memory, a plurality of sensors that detect an activity state of the user wearing, or having in its vicinity, the electronic device, and a display unit for displaying information to the user,
wherein in the server, the first processor reads out a program stored in the first memory to execute the following processes:
  receiving signals from the electronic device representing signals detected by the plurality of sensors;
  determining the activity state of the user based on the received signals;
  selecting one or more of sensors from the plurality of sensors at the electronic device on the basis of the determined activity state of the user; and
  transmitting to the electronic device the selection of the one or more of the sensors,
wherein in the electronic device, the second processor reads out a program stored in the second memory to execute the following processes:
  generating the signals detected by the plurality of sensors;
  transmitting the signals representing the signals detected by the plurality of sensors to the server;
  receiving from the server the selection of the one or more of the sensors; and
  causing multiple pieces of information sensed by said selected one or more of the sensors to be displayed on the display unit, and
wherein the display unit has a plurality of display regions respectively displaying said multiple pieces of information on the display unit,
wherein the plurality of sensors include a first sensor that obtains information pertaining to an exercise state of the user and a second sensor that obtains information pertaining to an external environment of the user,
wherein the first processor determines the exercise state by selecting one of a plurality of preset exercise states on the basis of the information obtained by the first sensor, said plurality of preset exercise states including at least one of resting, walking, running, and riding a bike,
wherein the first processor determines the external environment of the user by selecting one of a plurality of preset external environment states on the basis of the information obtained by the second sensor, said plurality of preset external environment states including at least one of on-a-road, mountain, and altitude increasing-decreasing states,
wherein the first processor determines the activity state of the user by selecting one of a plurality of preset activity states on the basis of the selected one of the preset exercise states and the selected one of the preset external environment states, said plurality of preset activity states including at least one of walking, hiking, trail running, cycling on road, and mounting biking,
wherein said plurality of preset exercise states, said plurality of preset external environment states, and said plurality of preset activity states are stored in said first memory or a separate memory, and
wherein the first processor selects said one or more of sensors from the plurality of sensors on the basis of the determined activity state as being associated with the determined activity state of the user, by referring to a lookup table that defines predetermined associations between the plurality of preset activity states and the plurality of sensors respectively corresponding thereto, the lookup table being stored in said first memory or said separate memory.

8. The system according to claim 7,
wherein said plurality of preset exercise states includes all of resting, walking, running, and riding a bike,
wherein said plurality of preset external environment states includes all of on-a-road, mountain, and altitude increasing-decreasing states, and
wherein said plurality of preset activity states includes all of walking, hiking, trail running, cycling on road, and mounting biking.

9. A method for selectively communicating sensed information to a user by a wearable electronic device, the electronic device having a memory; a processor connected to the memory, a plurality of sensors that detects an activity state of the user, and a display unit for displaying information to the user, the method comprising, via the processor:
  receiving signals from the plurality of sensors;
  determining the activity state of the user based on the received signals;
  selecting one or more of sensors from the plurality of sensors on the basis of the determined activity state;
  deriving, on the basis of the determined activity state, multiple pieces of information to be communicated to the user, said multiple pieces of information to be communicated to the user being derived from the signals from said selected one or more of the sensors; and causing said derived multiple pieces of information to be displayed on the display unit, and wherein the display unit has a plurality of display regions respectively displaying said multiple pieces of information on the display unit, wherein the plurality of sensors include a first sensor that obtains information pertaining to an exercise state of the user and a second sensor that obtains information pertaining to an external environment of the user, wherein the determining of the activity state of the user includes:

determining the exercise state by selecting one of a plurality of preset exercise states on the basis of the information obtained by the first sensor, said plurality of preset exercise states including at least one of resting, walking, running, and riding a bike, determining the external environment of the user by selecting one of a plurality of preset external environment states on the basis of the information obtained by the second sensor, said plurality of preset external environment states including at least one of on-a-road, mountain, and altitude increasing-decreasing states, and determining the activity state of the user by selecting one of a plurality of preset activity states on the basis of the selected one of the preset exercise states and the selected one of the preset external environment states, said plurality of preset activity states including at least one of walking, hiking, trail running, cycling on road, and mounting biking, wherein said plurality of preset exercise states, said plurality of preset external environment states, and said plurality of preset activity states are stored in said memory or a separate memory, and wherein said one or more of sensors is selected from the plurality of sensors on the basis of the determined activity state and said multiple pieces of information displayed to the user is derived as being associated with the determined activity state of the user, by referring to a lookup table that defines predetermined associations between the plurality of preset activity states and the multiple pieces of information respectively corresponding thereto, the lookup table being stored in said memory or said separate memory.

10. The method according to claim 9, wherein said plurality of preset exercise states includes all of resting, walking, running, and riding a bike, wherein said plurality of preset external environment states includes all of on-a-road, mountain, and altitude increasing-decreasing states, and wherein said plurality of preset activity states includes all of walking, hiking, trail running, cycling on road, and mounting biking.

11. A non-transitory storage medium having stored therein instructions executable by a processor in a wearable electronic device having a plurality of sensors that detects an activity state of a user and a display unit for displaying information to the user, said instructions in the storage medium causing the processor to perform the following:

receiving signals from the plurality of sensors;

determining the activity state of the user based on the received signals;

selecting one or more of sensors from the plurality of sensors on the basis of the determined activity state;

deriving, on the basis of the determined activity state, multiple pieces of information to be communicated to the user, said multiple pieces of information to be communicated to the user being derived from the signals from said selected one or more of the sensors; and causing said derived multiple pieces of information to be displayed on the display unit, wherein the display unit has a plurality of display regions respectively displaying said multiple pieces of information on the display unit, wherein the plurality of sensors include a first sensor that obtains information pertaining to an exercise state of the user and a second sensor that obtains information pertaining to an external environment of the user, wherein the determining of the activity state of the user includes:

determining the exercise state by selecting one of a plurality of preset exercise states on the basis of the information obtained by the first sensor, said plurality of preset exercise states including at least one of resting, walking, running, and riding a bike, determining the external environment of the user by selecting one of a plurality of preset external environment states on the basis of the information obtained by the second sensor, said plurality of preset external environment states including at least one of on-a-road, mountain, and altitude increasing-decreasing states, and determining the activity state of the user by selecting one of a plurality of preset activity states on the basis of the selected one of the preset exercise states and the selected one of the preset external environment states, said plurality of preset activity states including at least one of walking, hiking, trail running, cycling on road, and mounting biking, wherein said plurality of preset exercise states, said plurality of preset external environment states, and said plurality of preset activity states are stored in said memory or a separate memory, and wherein said one or more of sensors is selected from the plurality of sensors on the basis of the determined activity state and said multiple pieces of information displayed to the user is derived as being associated with the determined activity state of the user, by referring to a lookup table that defines predetermined associations between the plurality of preset activity states and the multiple pieces of information respectively corresponding thereto, the lookup table being stored in said memory or said separate memory.

12. The non-transitory storage medium according to claim 11, wherein said plurality of preset exercise states includes all of resting, walking, running, and riding a bike, wherein said plurality of preset external environment states includes all of on-a-road, mountain, and altitude increasing-decreasing states, and wherein said plurality of preset activity states includes all of walking, hiking, trail running, cycling on road, and mounting biking.

13. An electronic device, comprising:

a memory;

a processor connected to the memory and configured to receive a plurality of types of information respectively sensed by a plurality of sensors that detect an activity state of a user wearing, or having in its vicinity, the electronic device; and a display unit for displaying information to the user, wherein the processor reads out a program stored in the memory to perform the following processes:

receiving the plurality of types of information respectively sensed by the plurality of sensors;

determining the activity state of the user based on the received plurality of types of information;

selecting two or more of the plurality of types of information on the basis of the determined activity state; and causing said selected two or more of the plurality of types of information to be displayed on the display unit, and wherein the display unit has a plurality of display regions respectively displaying said two or more of the plurality of types of information on the display unit, wherein the plurality of sensors include a first sensor that obtains information pertaining to an exercise state of the user and a second sensor that obtains information pertaining to an external environment of the user, wherein the processor determines the exercise state by selecting one of a plurality of preset exercise states on the basis of the information obtained by the first sensor, said plurality of preset exercise states including at least one of resting, walking, running, and riding a bike, wherein the processor determines the external environment of the user by selecting one of a plurality of preset external environment states on the basis of the information obtained by the second sensor, said plurality of preset external environment states including at least one of on-a-road, mountain, and altitude increasing-decreasing states, wherein the processor determines the activity state of the user by selecting one of a plurality of preset activity states on the basis of the selected one of the preset exercise states and the selected one of the preset external environment states, said plurality of preset activity states including at least one of walking, hiking, trail running, cycling on road, and mounting biking, wherein said plurality of preset exercise states, said plurality of preset external environment states, and said plurality of preset activity states are stored in said memory or a separate memory, and wherein the processor selects said two or more of the plurality of types of information on the basis of the determined activity state as being associated with the determined activity state of the user, by referring to a lookup table that defines predetermined associations between the plurality of preset activity states and the plurality of types of information respectively corresponding thereto, the lookup table being stored in said memory or said separate memory.

14. The electronic device according to claim 13, wherein the plurality of types of information includes at least some of pressure, altitude, speed, position, direction, and heart rate.

15. The electronic device according to claim 13, wherein said plurality of preset exercise states includes all of resting, walking, running, and riding a bike, wherein said plurality of preset external environment states includes all of on-a-road, mountain, and altitude increasing-decreasing states, and wherein said plurality of preset activity states includes all of walking, hiking, trail running, cycling on road, and mounting biking.

\* \* \* \* \*